United States Patent [19]

Stephen et al.

[11] 4,156,179

[45] May 22, 1979

[54] ELECTRICAL CONDUCTIVITY INDICATORS AND/OR METHODS OF USING SAME

[75] Inventors: Stuart J. Stephen, Waihou; Thomas D. Millar, Hamilton, both of New Zealand

[73] Assignee: AHI Operations Limited, Auckland, New Zealand

[21] Appl. No.: 769,192

[22] Filed: Feb. 16, 1977

[51] Int. Cl.² .......................................... G01N 27/42
[52] U.S. Cl. .......................... 324/30 R; 324/DIG. 1; 119/14.14
[58] Field of Search .................. 324/30 R, 62, 30 B, 324/29, 133, DIG. 1; 119/14.14, 14.15, 14.16

[56] References Cited

U.S. PATENT DOCUMENTS

| 2,898,549 | 8/1959 | Miller | 324/30 B |
| 3,003,103 | 10/1961 | Smals et al. | 324/30 R |
| 3,664,306 | 5/1972 | Quayle | 324/30 B |
| 4,020,414 | 4/1977 | Paredes | 324/133 |

Primary Examiner—M. Tokar
Attorney, Agent, or Firm—Holman & Stern

[57] ABSTRACT

An electrical conductivity indicator has a bridge circuit which is supplied from a source of electronic oscillations preferably successive half cycles being of reverse polarity and having electrodes in a cup arranged to be hand held below the teat of a cow so that the presence or absense of Mastitis infection is indicated by the variations in electrical conductivity of the milk held in the cup.

10 Claims, 4 Drawing Figures

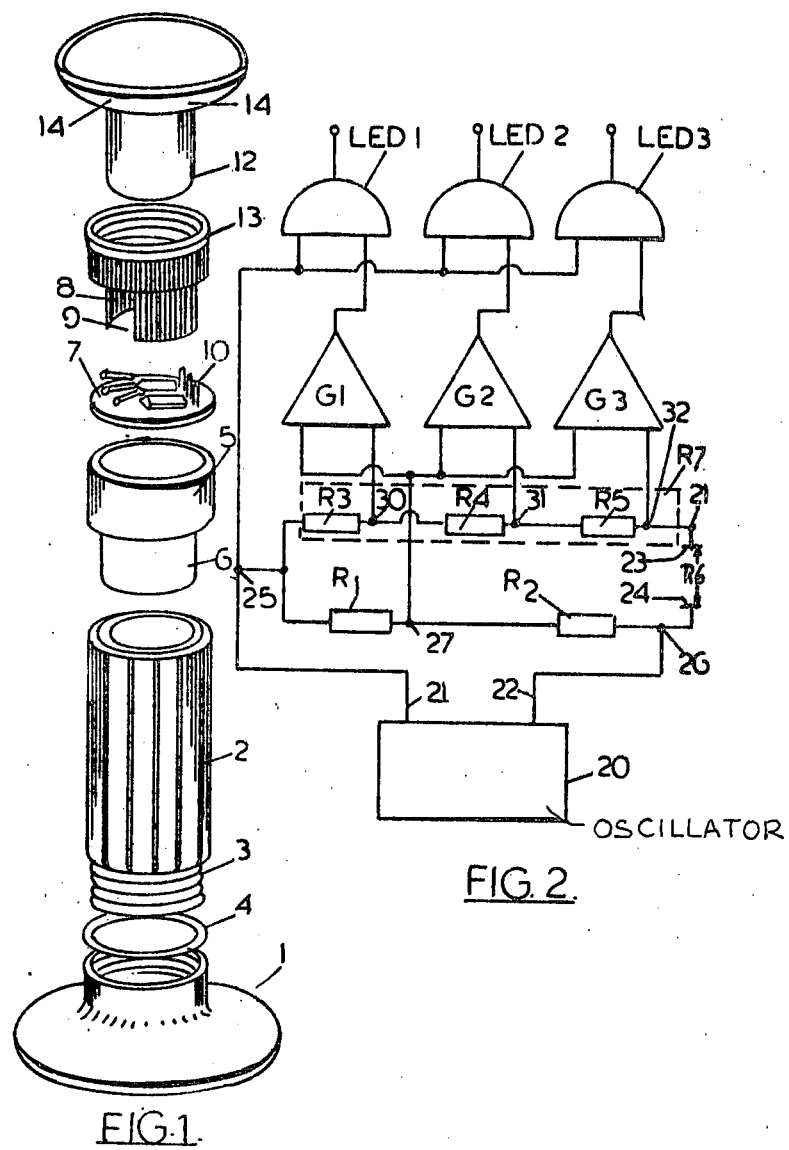

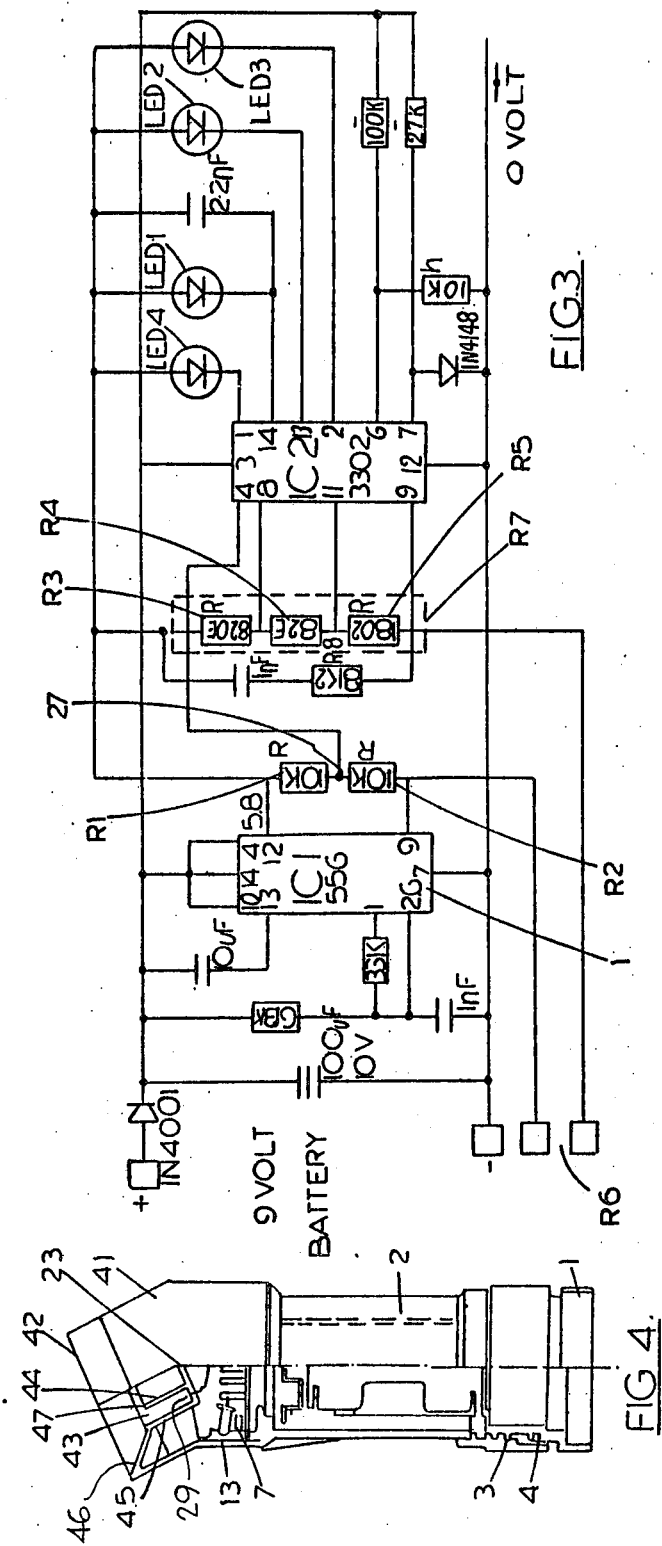

ELECTRICAL CONDUCTIVITY INDICATORS AND/OR METHODS OF USING SAME

This invention relates to electrical conductivity indicators and/or methods of using same to detect mastitis infection in cows.

It is an object of the present invention to provide an electrical conductivity indicator and/or method of using same which will provide the public with a useful choice.

Accordingly in one aspect the invention consists in an electrical conductivity indicator comprising a source of electrical oscillations a bridge circuit including in one arm thereof electrodes arranged so that in use the electrodes are bridged by a liquid the electrical conductivity of which is to be indicated, two terminals of said bridge circuit being connected to said source, said bridge circuit being also connected to an indicating means which indicate changes in electrical conductivity of liquid bridging said electrodes.

In a further aspect the invention consists in a method of detecting mastitis infection in cows using an electrical conductivity indicator having a container for milk from the cow being tested, electrodes in said container and an electronic circuit to indicate the electrical conductivity of milk in the container said method comprising the steps of expressing milk from an individual teat of a cow being tested into said container, testing the conductivity of the milk, emptying the container and repeating said steps.

To those skilled in the art to which this invention relates, many changes in construction and widely differing embodiments and applications of the invention will suggest themselves without departing from the scope of the invention as defined in the appended claims. The disclosures and the description herein are purely illustrative and are not intended to be in any sense limiting.

One preferred form of the invention and modifications thereof will now be described with reference to the accompanying drawings in which, FIG. 1 is an exploded view of an electrical conductivity indicator according to the invention, FIG. 2 is a block circuit diagram of the electrical conductivity indicator incorporating the invention, FIG. 3. is a detailed circuit diagram of an electrical conductivity indicator according to the invention, and FIG. 4 is as FIG. 1 but showing some modifications of the parts thereof.

Referring to the drawings an electrical conductivity indicator for use in indicating the electrical conductivity of milk from an individual teat of a cow is shown. The device shown in FIG. 1 is intended to be held in the hand and to be battery powered. Accordingly the device comprises a base 1 and a tube 2 which forms a battery case the tube 2 being screwed by a thread 3 into the base 1 and an O ring 4 being provided so that a substantially water tight seal may be provided between the base 1 and the tube 2. A switch (not shown) is operated by screwing the tube onto and away from the base 1. A transparent or translucent electronic case 5 for example clear polysulfone is provided the spigot 6 being solvent jointed to the battery case 2 and the electronics are mounted on a plate 7 which may for example include a printed circuit and the necessary electronic components (to be described shortly) mounted thereon. A mask 8 is solvent jointed to the case 5 and a gap 9 in the mask 8 is positioned so that light emitting diodes 10 can be seen through the gap 9 and through the clear wall of the case 5. A removable container in the form of a cup 11 is provided and for example a bayonet lock is provided between the spigot 12 and the socket 13. The container 11 contains a pair of electrodes 23 and 24 a suitable distance apart and arranged to be submerged in a liquid, e.g., milk placed in the container or cup 11.

Referring now to FIG. 2 a source of electrical oscillations referenced 20 is provided having output terminals 21 and 22. To avoid polarisation troubles at the electrodes 23 and 24 the oscillations are preferably such that successive half waves have reverse, i.e., alternating polarity. The output terminals 21 and 22 are connected to terminals 25 and 26 of a Wheatstone or Wien bridge circuit comprises fixed resistors R1 and R2 forming two of the arms of the bridge, a plurality of resistors R3, R4 and R5 which together form a combined resistance R7 forming a third arm of the bridge and the electrodes 23 and 24 which together with the liquid between them in use provide the fourth arm R6 of the bridge.

To give indications of the balance of the bridge circuit, i.e., to give indications of the electrical conductivity of liquid between the electrodes 23 and 24 and indicating means could be placed between terminals 27, i.e., the junction between R1 and R2 and 28, i.e., the junction between R6 and R7. Preferably however a plurality of voltage comparator circuits which when energised illuminate light emitting diodes LED 1, LED 2, and LED 3 are provided in conjunction with the resistors R3 R4 and R5 by the use of gate circuits G1, G2 and G3. The electrical conductivity of milk increases with the presence of mastitis therein and accordingly the conductivity of the liquid between probes 23 and 24 is dependent on, firstly the physical dimension and spacing of the electrodes 23 and 24 and secondly the parameters of the components of the circuit of FIG. 2. These of course can be designed to give satisfactory operation which will vary according to the presence or absence of mastitis in the milk in the container 11 as will be described further shortly. Variations in the conductivity will result in one or more of the light emitting diodes being illuminated according to the voltage and circuit operating conditions applied to G1, G2, and G3 as between terminal 27 and junctions 30,31 and 32 respectively. In this way an indication as to the level of conductivity of milk in the container 11 and consequently the level of mastitis present can be given.

The use of the device shown in FIGS. 1 and 2 is as follows:

An operator having assembled the apparatus with the battery in position and as stated it is intended that the battery will be switched on by screwing the tube 2 more tightly onto the base 1, suitable contacts being provided so that this makes contact between the battery and the electronic circuit of FIG. 2. The operator then expresses the milk from one teat of a cow into the container 11 and preferably this expressed milk is the fore milk which is usually wasted when the operator is washing the cow's udder preparatory to machine milking. On the milk covering the electrodes 23 and 24 the light emitting diodes LED 1, LED 2 and LED 3 are illuminated or not depending firstly on the presence of mastitis in the milk, and secondly on the degree of presence; both of these being dependent on the conductivity of milk. Accordingly an indication of mastitis level is quickly and rapidly given. After testing an individual teat the milk may be discarded and a further sample taken with if necessary intermediate washing of the container 11. Thus milk from individual quarters or teats of a cow can be tested quickly and easily so that sub clinical mastitis can be detected and preventative steps taken.

In FIG. 3 there is shown a circuit similar to that of FIG. 2 and carrying similar references but in which the details of circuit integers are given the particular integers comprising integrated circuits as shown in the diagram.

LED 4 and its associated circuitry indicates battery condition in use.

Referring to FIG. 4 the indicator shown in that figure is similar to that shown in FIG. 1 but there is provided an angled spacer 41 arranged so that when the cup periphery 42 is horizontally disposed a users hand on the tube 2 is at a convenient angle and disposition. The cup 43 has two compartments one an inner cylindrical compartment 44 containing one electrode 23 and the other an outer annular compartment 45 containing the second electrode 29. A frusto conical section 46 is joined to the upper edge of the compartment 45. This arrangement is such that the milk level must be above the wall 47 of inner compartment before the liquid circuit is complete and variations in milk levels between the wall 47 and the edge 42 do not cause material variation of the conductivity readings given. The advantages of such circuitry are considerable.

We claim:

1. A mastitis detector for the detection of mastitis in a cow, said detector comprising:
    a container for receiving milk to be tested, said container receving milk from an individual teat of said cow, said container comprising an open mouthed cup, and a wall lower in height than the height of said cup, dividing said cup into a central inner chamber and an outer chamber therearound;
    an electrode provided in each chamber;
    energising means to supply an electrical potential to said electrodes; and
    an electrical conductivity indicator connected to said electrodes and said energising means for measuring electrical conductivity of said milk when sufficient milk is in said container to submerge at least a portion of said wall.

2. A mastitis detector as claimed in claim 1, wherein said wall is a cylindrical wall.

3. A mastitis detector as claimed in claim 1, wherein said container includes means mounting said cup above said electrical conductivity indicator and said energising means, and permitting hand-held operation.

4. A mastitis detector as claimed in claim 3 wherein said energising means is a battery and said means mounting said cup includes case means for mounting said electrical battery and said electrical conductivity indicator in a water tight case.

5. A mastitis detector as claimed in claim 1 wherein said cup has a lower cylindrical portion surmounted by a frustum of a cone forming said open mouthed portion.

6. A mastitis detector as claimed in claim 1 wherein said electrical conductivity indicator comprises:
    a source of electrical oscillation;
    a bridge circuit including in one arm thereof connections to said electrodes; and
    means connecting said bridge circuit to said source, and to at least one indicating means which indicate changes in electrical conductivity of the milk.

7. A mastitis detector as claimed in claim 6 wherein said indicator includes a plurality of voltage comparator circuits for activating said indicating means in response to the electrical conductivity of the milk.

8. A mastitis detector as claimed in claim 7 wherein each of said indicating means comprises a light emitting diode.

9. A mastitis detector as claimed in claim 8 wherein a plurality of light emitting diodes comprise said indicator and includes means for illuminating a greater number of diodes to indicate a greater conductivity.

10. A method of detecting mastitis in cows using an electrical conductivity indicator having an open mouthed container for milk, said container comprising an open mouthed cup divided into two chambers separated by a wall so that an outer chamber is formed around a central inner chamber, said wall being lower in height than the height of the cup, an electrode being provided in each chamber and an electronic circuit to indicate the electrical conductivity of milk in the container, said method comprising the steps of:
    expressing milk from an individual teat of a cow being tested into said container until said milk covers at least part of said wall; and
    testing the conductivity of the milk.

* * * * *